United States Patent
Osswald et al.

Patent Number: 5,700,807
Date of Patent: Dec. 23, 1997

[54] ENDOTHELIN RECEPTOR ANTAGONISTS

[75] Inventors: Mathias Osswald, Swingenberg; Dieter Dorsch, Ober-Ramstadt; Werner Mederski, Erzhausen; Claudia Wilm, Mühltal; Claus J. Schmitges, Darmstadt; Maria Christadler, Rodermark, all of Germany

[73] Assignee: Merck Patent Gesellschaft mit Beschrankter Haftung, Darmstadt, Germany

[21] Appl. No.: 687,922

[22] Filed: Jul. 26, 1996

[30] Foreign Application Priority Data

Jul. 28, 1995 [DE] Germany ............ 195 27 568.3

[51] Int. Cl.⁶ .............. C07D 491/048; C07D 513/04; A61K 31/395
[52] U.S. Cl. .............. 514/291; 546/80; 546/89; 546/92
[58] Field of Search .............. 546/80, 89, 92; 514/291

[56] References Cited

U.S. PATENT DOCUMENTS

| | | | |
|---|---|---|---|
| 4,985,422 | 1/1991 | North et al. | 546/89 |
| 5,292,740 | 3/1994 | Burri et al. | 514/256 |

FOREIGN PATENT DOCUMENTS

| | | | |
|---|---|---|---|
| 617001 | 3/1994 | European Pat. Off. | A61K 31/19 |
| 93/0879 | 3/1992 | WIPO | A61K 31/19 |
| 93/08799 | 5/1993 | WIPO | C07D 471/04 |
| 94/14434 | 12/1993 | WIPO | A61K 31/40 |
| 95/33748 | 12/1995 | WIPO | A61K 31/19 |

OTHER PUBLICATIONS

Rose, Ulrich, "5–Oxo–1,4–dihydroindenopyridines: Calcium Modulators . . . " J. Heterocyclic Chem., 27, 1990, pp. 237–242.

*Primary Examiner*—Robert T. Bond
*Attorney, Agent, or Firm*—Millen, White, Zelano & Branigan, P.C.

[57] ABSTRACT

Novel compounds of the formula

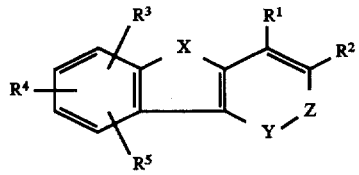

in which

—Y—Z—, $R^1$, $R^2$, $R^3$, $R^4$, $R^5$ and X have the meaning indicated and their salts show endothelin receptor-antagonistic properties.

16 Claims, No Drawings

ENDOTHELIN RECEPTOR ANTAGONISTS

The invention relates to compounds of the formula I

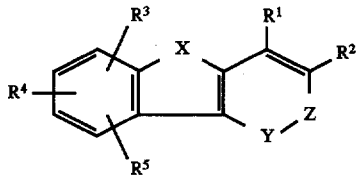

in which

—Y—Z— is —NR$^7$—CO—, —N=C(OR$^7$)— or —N=CR$^8$—,

R$^1$ is Ar,

R$^2$ is COOR$^6$, CN, 1H-tetrazol-5-yl or CONHSO$_2$Ar,

R$^3$, R$^4$ and R$^5$ in each case independently of one another are R$^6$, OR$^6$, S(O)$_m$R$^6$, Hal, NO$_2$, NR$^6$R$^{6'}$, NHCOR$^6$, NHSO$_2$R$^6$, OCOR$^6$, COOR$^6$ or CN, R$^6$ and R$^{6'}$ in each case independently of one another are H, alkyl having 1 to 6 C atoms, benzyl or phenyl, R$^7$ is (CH$_2$)$_n$Ar, R$^8$ is Ar or OAr Ar are in each case independently phenyl which is unsubstituted or mono-, di- or trisubstituted by R$^9$, R$^{10}$ or R$^{11}$, or unsubstituted naphthyl or a

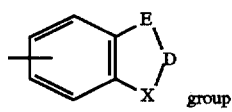 group which is unsubstituted or mono- or disubstituted in the phenyl moiety by R$^9$ or R$^{10}$, or a

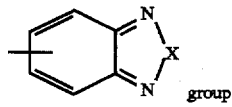 group which is unsubstituted or mono- or disubstituted in the cyclohexadienyl moiety by R$^9$ or R$^{10}$, R$^9$, R$^{10}$ and R$^{11}$ in each case independently of one another are R$^6$, OR$^6$, Hal, CF$_3$, OCF$_3$, OCHF$_2$, OCH$_2$F, NO$_2$, NR$^6$R$^{6'}$, NHCOR$^6$, CN, NHSO$_2$R$^6$, COOR$^6$, COR$^6$, CONHSO$_2$Ar, O(CH$_2$)$_n$R$^2$, O(CH$_2$)$_n$OR$^6$ or S(O)$_m$R$^6$, E is CH$_2$, S or O, D is carbonyl or [C(R$^6$R$^{6'}$)]$_n$, Hal is F, Cl, Br or I, X is C or S m is 0, 1 or 2 n is 1 or 2, and their salts.

Similar compounds having indan and indene parent structures are disclosed in WO 93/08799, those with indole systems are disclosed in WO 94/14434, pyrimidine derivatives are disclosed in EP 0 526 708 A1 and phenyl and naphthyl compounds are disclosed in EP 0 617 001 A1.

The invention is based on the object of finding novel compounds having useful properties, in particular those which can be used for the production of medicaments.

It has been found that the compounds of the formula I and their salts have very useful pharmacological properties combined with good tolerability. In particular, they show endothelin receptor-antagonistic properties and can therefore be employed for the treatment of illnesses such as hypertension, cardiac insufficiency, coronary heart disease, renal, cerebral and myocardial ischaemia, renal insufficiency, cerebral infarct, subarachnoid haemorrhage, arteriosclerosis, pulmonary high blood pressure, inflammations, asthma, prostate hyperplasia, endotoxic shock and in complications after the administration of substances such as, for example, cyclosporin, and also other illnesses associated with endothelin activities.

Inter alia, the compounds show a high affinity for the endothelin subreceptors ET$_A$ and ET$_B$. These effects can be determined by customary in vitro or in vivo methods, such as described, for example, by P. D. Stein et al., J. Med. Chem. 37, 1994, 329–331 and E. Ohlstein et al., Proc. Natl. Acad. Sci. USA 91, 1994, 8052–8056.

A suitable method for the determination of the hypotensive effect is described, for example, by M. K. Bazil et al., J. Cardiovasc. Pharmacol. 22, 1993, 897–905 and J. Lange et al., Lab Animal 20, 1991, Appl. Note 1016.

The compounds of the formula I can be employed as pharmaceutically active compounds in human and veterinary medicine, in particular for the prophylaxis and/or therapy of cardiac, circulatory and vascular illnesses, especially hypertension and cardiac insufficiency.

The invention relates to the compounds of the formula I and their salts and to a process for the preparation of these compounds and their salts, characterized in that (a) for the preparation of a compound of the formula I in which —Y—Z— is —NR$^7$—CO— or —N=C(OR$^7$)—, a compound of the formula II

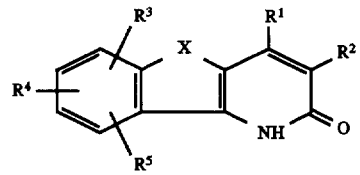

in which

R$^1$, R$^2$, R$^3$, R$^4$, R$^5$ and X have the meanings indicated above, is reacted with a compound of the formula III

R$^7$—Q     III in which

Q is Cl, Br, I or a free or reactively functionally modified OH group and

R$^7$ has the meaning indicated above, or in that (b) for the preparation of a compound of the formula I in which —Y—Z— is —N=C(Ar)—, a compound of the formula IV

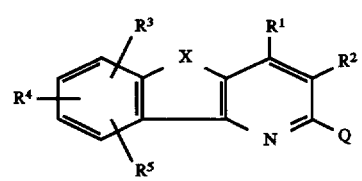

in which

Q is Cl, Br or I and

R$^1$, R$^2$, R$^3$, R$^4$, R$^5$ and X have the meanings indicated above, is reacted with a boron compound of the formula V Ar—BLL'    V in which L and L' in each case independently of one another are OH, OCH$_3$, OC$_2$H$_5$ or OC$_3$H$_7$, and Ar has the meaning indicated above, or in that c) for the preparation of a compound of the formula I, in which —Y—Z— is —N=C(OAr)—, a compound of the formula IV in which Q is Cl, Br, I or a reactively functionally modified OH group, is reacted with a compound of the formula VI Ar—OH    VI and/or in that in a compound of the formula I one or more radicals R$^1$, R$^2$, R$^3$, R$^4$ and/or R$^5$ are converted into one or more radicals R$^1$, R$^2$, R$^3$, R$^4$ and/or R$^5$ by, for example, i) reducing a nitro group to an amino group,
ii) hydrolyzing an ester group to a carboxyl group,
iii) converting an amino group into an alkylated amine by reductive amination,
iv) converting a carboxyl group into a sulfonamidocarbonyl group and/or converting a base or acid of the formula I into one of its salts.

The meanings of all radicals which occur several times, such as, for example, R$^4$ and Ar, are independent of one another.

In the above formulae, alkyl has 1 to 6, preferably 1, 2, 3 or 4 C atoms. Alkyl is preferably methyl, furthermore ethyl, propyl, isopropyl, butyl, isobutyl, sec-butyl or tert-butyl, and furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-1,3-2,2-, 2-3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

E is in particular CH$_2$ or O, and furthermore also S.

D is in particular carbonyl and CH$_2$.

X is preferably O, and furthermore preferably S.

m is in particular O, and furthermore preferably also 1 and 2.

n is preferably 1, and furthermore preferably 2.

Hal is preferably F, Cl or Br, but also I.

Ar is unsubstituted, preferably—as indicated—monosubstituted phenyl, particularly preferably phenyl, o-, m- or p-tolyl, o-, m- or p-ethylphenyl, o-,m- or p-propylphenyl, o-, m- or p-isopropylphenyl, o-, m- or p-tert-butylphenyl, o-, m- or p-triflouromethylphenyl, o-, m- or p-hydroxyphenyl, o-, m- or p-nitrophenyl, o-, m- or p-aminophenyl, o-, m- or p- (N-methylamino)phenyl, o-, m- or p-acetamidophenyl, o-, m- or p-(trifluoromethoxy) phenyl, o-, m- or p-cyanophenyl, o-, m- or p-methoxyphenyl, o-, m- or p-ethoxyphenyl, o-, m- or p-carboxyphenyl, o-, m- or p-methoxycarbonylphenyl, o-, m- or p-ethoxy-carbonylphenyl, o-, m- or p-benzyloxycarbonylphenyl, o-, m- or p-(carboxymethyloxy)phenyl, o-, m- or p-(methoxycarbonylmethyloxy)phenyl, o-, m- or p-(methoxycarbonylethyloxy)phenyl, o-, m- or p-(N,N-dimethylamino)phenyl, o-, m- or p-(N-ethylamino) phenyl, o-, m- or p-(N,N-diethylamino)phenyl, o-, m- or p-fluorophenyl, o-, m- or p-bromophenyl, o-, m- or p-chlorophenyl, o-, m- or p-(difluoromethoxy)phenyl, o-, m- or p-(fluoromethoxy)phenyl, o-, m- or p-formylphenyl, o-, m- or p-acetylphenyl, o-, m- or p-propionylphenyl, o-, m- or p-butyrylphenyl, o-, m- or p-pentanoylphenyl, o-, m- or p-(phenylsulfonamidocarbonyl)phenyl, o-, m- or p-phenoxyphenyl, o-, m- or p-methylthiophenyl, o-, m- or p-methylsulfinylphenyl, o-, m- or p-methylsulfonylphenyl, o-, m- or p-benzyloxyphenyl, o-, m- or p-cyanomethyloxyphenyl, further preferably 2,3-methylenedioxyphenyl, 3,4-methylenedioxyphenyl, 2,3-ethylenedioxyphenyl, 3,4-ethylenedioxyphenyl, 2,3-(2-oxomethylenedioxy) phenyl, 2,3-, 2,4-2,5-, 2,6-, 3,4- or 3,5-(difluoromethoxy)(carboxymethyloxy)phenyl, 2,3-, 2,4-, 2,5-, 2,6-, 3,4- or 3,5-methoxy-(carboxymethyloxy)phenyl, 2,3-, 2,4-, 2,5-, 2,6-, 3,4- or 3,5-hydroxy-(carboxymethyloxy)phenyl.

Ar is further preferably 2,3-dihydrobenzofuranyl, 2,3-dihydro-2-oxofuranyl, 1,3-dithiaindanyl, 2,1,3-benzothiadiazolyl, 2,1,3-benzoxadiazolyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chlorophenyl, 2-bromo-3-methyl-, 2-bromo-4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2,4- or 2,5-dinitrophenyl, 2,5- or 3,4-diemethoxy-phenyl, 3-nitro-4-chlorophenyl, 2-amino-3-chloro-, 2-amino-4-chloro- , 2-amino-5-chloro or 2-amino-6-chloro-phenyl, 2-nitro-4-N, N-dimethylamino- or 3-nitro-4-N,N-dimethylaminophenyl, 3-carboxy-2-methoxy-, 3-carboxy-4-methoxy- or -carboxy-5-methoxyphenyl, 2,3,4-, 2,3,5-2,3,6-, 2,4,6- or 3,4,5-trichlorophenyl, 2,4,6-tri-tertbutylphenyl, and furthermore preferably 2-nitro-4-(trifluoromethyl)phenyl, 3,5-di-(trifluoromethyl)phenyl, 2,5-dimethylphenyl, 2-hydroxy-3, 5-dichlorophenyl, 2-fluoro-5- or 4-fluoro-3-(trifluoromethyl)phenyl, 4-chloro-2- or 4-chloro-3-(trifluoromethyl)-, 2-chloro-4- or 2-chloro-5-(trifluoromethyl)phenyl, 4-bromo-2- or 4-bromo-3-(trifluoromethyl)phenyl, p-iodophenyl, 2-nitro-4-methoxyphenyl, 2,5-dimethoxy-4-nitrophenyl, 3,5-dicarboxyphenyl, 2-chloro-3-nitro-5-carboxyphenyl, 4-chloro-3-carboxyphenyl, 2-methyl-5-nitrophenyl, 2,4-dimethyl-3-nitrophenyl, 3,6-dichloro-4-aminophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 3-bromo-6-methoxyphenyl, 3-chloro-6-methoxyphenyl, 3-chloro-4-acetamidophenyl, 4-hydroxy-3-carboxyphenyl, 2-methoxy-5-methylphenyl or 2,4,6-triisopropylphenyl, and furthermore naphthyl.

The radical R$^2$ is preferably carbomethoxy, carboethoxy, carbopropoxy, carbobutoxy, carbobenzyloxy, and furthermore cyano, 1H-tetrazol-5-yl or phenylsulfonamidocarbonyl, but is particularly preferably carboxyl.

The radicals R$^3$, R$^4$ and R$^5$ are in each case independently of one another preferably H, methyl, ethyl, propyl, isopropyl, butyl, isobutyl, sec-butyl or tert-butyl, benzyl, F, Cl, Br, methoxy, ethoxy, phenoxy, benzyloxy, nitro or cyano, and amino, methylamino, dimethylamino, ethylamino, diethylamino, acetylamino, propionylamino, butyrylamino, methylsulfonamido, ethylsulfonamido, phenylsulfonamido, methylcarbonyloxy, ethylcarbonyloxy, phenylcarbonyloxy, methyloxycarbonyl, ethyloxycarbonyl, methylthio, ethylthio, propylthio, methylsulfinyl, ethylsulfinyl, phenylsulfinyl, methylsulfonyl, ethylsulfonyl or phenylsulfonyl are furthermore preferred.

The compounds of the formula I can have one or more chiral centers and therefore occur in various stereoisomeric forms. The formula I embraces all these forms.

The invention accordingly relates in particular to those compounds of the formula I in which at least one of the radicals mentioned has one of the preferred meanings indicated above. Some preferred groups of compounds can be expressed by the following subformulae Ia to Ig, which correspond to the formula I and in which the radicals not described in greater detail have the meaning indicated in the formula I, but in which in Ia —Y—Z— is —NR$^7$—CO— or —N=C(OR$^7$)—;

in Ib —Y—Z— is —N=CR$^8$—;

In Ic —Y—Z— is —NR$^7$—CO— and
X is O;

In Id —Y—Z— is —NR$^7$—CO—,
X is O and

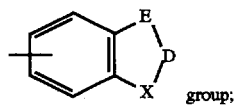

Ar is a in Ie —Y—Z— is —N=CR$^8$—,
R$^8$ is Ar,
Ar is phenyl which is mono-, di- or trisubstituted by R$^9$, R$^{10}$ or R$^{11}$ and
X is O;

in If X is S;
—Y—Z— is —NR$^7$—CO—
R$^7$ is CH$_2$Ar and

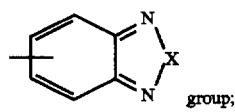

Ar is a
in Ig —Y—Z— is —N=CR$^8$—
X is O

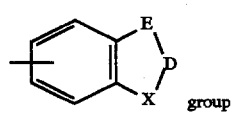

Ar is a
and
R$^8$ is OAr.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart; but in particular in WO 94/14434), namely under reaction conditions which are known and suitable for the reactions mentioned. Use can also be made in this case of variants which are known per se but not mentioned here in greater detail.

If desired, the starting substances can also be formed in situ such that they are not isolated from the reaction mixture, but immediately reacted further to give the compounds of the formula I.

Compounds of the formula I can preferably be obtained by reacting compounds of the formula II with compounds of the formula III.

In the compounds of the formula III, Q is preferably Cl, Br, I or a reactively modified OH group such as alkylsulfonyloxy having 1–6 C atoms (preferably methylsulfonyloxy) or arylsulfonyloxy having 6–10 C atoms (preferably phenyl or p-tolylsulfonyloxy).

The reaction is generally carried out in an inert solvent, in the presence of an acid-binding agent, preferably of an alkali metal or alkaline earth metal hydroxide, carbonate or bicarbonate or of another salt of a weak acid of the alkali metals or alkaline earth metals, preferably of potassium, sodium, calcium or cesium. The addition of an organic base such as triethylamine, dimethylaniline, pyridine or quinoline or an excess of the amide components of the formula II or of the alkylating derivative of the formula III can also be favorable. Depending on the conditions used, the reaction time is from a few minutes to 14 days and the reaction temperature is from approximately 0° C. to 150° C., normally from 20° C. to 130° C.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate or mixtures of the solvents mentioned. The starting compounds of the formula II are generally novel. However, they can be prepared by methods known per se. Thus, for example, ethyl 1,2-dihydro-4-(4-methoxyphenyl)-2-oxobenzofuro[3,2-b]pyridine-3-carboxylate can be prepared from 3-amino-2-(4-methoxybenzoyl)benzofuran and diethyl malonate without or in the presence of an inert solvent. This expediently takes place at temperatures from about 0° C. to approximately 200° C.; the reaction is preferably carried out at from 30° C. to 80° C.

Suitable inert solvents are exemplified by those already mentioned above.

Compounds of the formula I can furthermore preferably be obtained by reacting compounds of the formula IV with compounds of the formula V.

In the compounds of the formula IV, Q is preferably Cl or Br but also I.

In the compounds of the formula V, L and L' preferably in each case independently of one another are OH, methoxy, ethoxy, propoxy or isopropoxy.

The reaction is generally carried out in an inert solvent, in the presence of a base and of a noble metal catalyst.

Depending on the conditions used, the reaction time is preferably from a few minutes to 14 days and the reaction temperature is preferably from approximately 0° C. to 150° C., normally from 20° C. to 130° C.

Suitable inert solvents and bases are exemplified by those already mentioned above.

Preferred noble metal catalysts are particularly palladium (0) catalysts, such as tetrakis(triphenylphosphine)palladium (0).

The starting compounds of the formula IV are generally novel. However, they can be prepared by methods known per se. Thus, for example, ethyl 2-chloro-4-(4-methoxyphenyl)benzofuro[3,2-b]pyridine-3-carboxylate can be prepared from ethyl 1,2-dihydro-4-(4-methoxyphenyl)-2-oxobenzofuro[3,2-b]pyridine-3-carboxylate using $POCl_3$. This is preferably carried out at temperatures from about 0° C. to approximately 200° C.; particularly preferably carried out at from 30° C. to 80° C.

Compounds of the formula I can furthermore preferably be obtained by reacting compounds of the formula IV with compounds of the formula VI.

In the compounds of the formula VI, Q is preferably Cl, Br, I or a reactively modified OH group.

The reaction is generally carried out in an inert solvent and with addition of one of the abovementioned bases.

It is furthermore possible to convert a compound of the formula I into another compound of the formula I by converting one or more radicals $R^1$, $R^2$, $R^3$, $R^4$ and/or $R^5$ into one or more other radicals $R^1$, $R^2$, $R^3$, $R^4$ and/or $R^5$, e.g., by reducing nitro groups, for example by hydrogenation on Raney nickel or Pd-carbon in an inert solvent such as methanol or ethanol, to amino groups and/or converting an ester group to a carboxyl group and/or converting an amino group into an alkylated amine by reductive amination and/or esterifying carboxyl groups by reaction with alcohols.

Free amino groups can furthermore be acylated in a customary manner using an acid chloride or anhydride or alkylated using an unsubstituted or substituted alkyl halide, expediently in an inert solvent such as dichloromethane or THF and/or in the presence of a base such as triethylamine or pyridine at temperatures from about −60° C. to +30° C.

If desired, in a compound of the formula I a functionally modified amino and/or hydroxyl group can be set free by solvolysis or hydrogenolysis according to customary methods. Thus, for example, a compound of the formula I which contains an $NHCOR^6$ or a $COOR^6$ group can be converted into the corresponding compound of the formula I which, instead of this, contains an $NH_2$ or an HOOC group. $COOR^6$ groups can be hydrolyzed, for example, with NaOH or KOH in water, water-THF or water-dioxane at temperatures preferably from about 0° C. to 100° C.

A base of the formula I can be converted into the associated acid addition salt using an acid, for example by reaction of equivalent amounts of the base and of the acid in an inert solvent such as ethanol and subsequent evaporation. For this reaction, suitable acids are in particular those which yield physiologically acceptable salts. Thus inorganic acids can be used, e.g., sulfuric acid, nitric acid, hydrohalic acids such as hydrochloric acid or hydrobromic acid, phosphoric acids such as orthophosphoric acid, sulfamic acid, and furthermore organic acids, in particular aliphatic, alicyclic, araliphatic, aromatic or heterocyclic mono- or polybasic carboxylic, sulfonic or sulfuric acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, and laurylsulfuric acid. Salts with physiologically unacceptable acids, e.g., picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts, using bases, (e.g., sodium or potassium hydroxide or carbonates).

The invention furthermore relates to the use of the compounds of the formula I and/or their physiologically acceptable salts for the production of pharmaceutical preparations, in particular by a non-chemical route. In this context, they can be brought into a suitable dose form together with at least one solid, liquid and/or semi-liquid excipient or auxiliary and, if appropriate, in combination with one or more further active compounds.

The invention furthermore relates to pharmaceutical preparations, comprising at least one compound of the formula I and/or one of its physiologically acceptable salts.

These preparations can be used as medicaments in human or veterinary medicine. Possible excipients are organic or inorganic substances which are suitable for enteral (e.g., oral), parenteral or topical administration and do not react with the novel compounds, for example, water, vegetable oils, benzyl alcohols, alkylene glycols, polyethylene glycols, glycerol triacetates, gelatin, carbohydrates such as lactose or starch, magnesium stearates, talc and petroleum jelly. Tablets, pills, coated tablets, capsules, powders, granules, syrups, juices or drops are used, in particular, for oral administration, suppositories for rectal administration, solutions, preferably oily or aqueous solutions, and furthermore suspensions, emulsions or implants for parenteral administration, and ointments, creams or powders for topical application. The novel compounds can also be lyophilized and the lyophilizates obtained used, for example, for the production of injection preparations. The preparations indicated can be sterilized and/or auxiliaries such as lubricants, preservatives, stabilizers and/or wetting agents, emulsifiers, salts for affecting the osmotic pressure, buffer substances, colorants, flavorings and/or one or more further active compounds, e.g., one or more vitamins.

The compounds of the formula I and their physiologically acceptable salts can be used in the control of illnesses, for example, treatment and/or prevention, in particular of hypertension and cardiac insufficiency.

In this connection, the substances according to the invention are generally preferably administered in doses of from approximately 1 to 500 mg, in particular from 5 to 100 mg per dose unit. The daily dose is preferably from approximately 0.02 to 10 mg/kg of body weight. The specific dose for each patient, however, depends on all sorts of factors, for example on the efficacy of the specific compound employed, on the age, body weight, general state of health, sex, on the diet, on the time and route of administration, and on the excretion rate, pharmaceutical substance combination and severity of the particular disorder to which the therapy applies. Oral administration is preferred.

Although the compounds belong to a new class of substances, they may be administered, for example, in a manner and in dosages analogous to ACE inhibitors such as captropril and enalapril.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German DE 195 27 568.3, are hereby incorporated by reference.

EXAMPLES

Hereinbefore and hereinafter, all temperatures are indicated in °C. In the following examples, "customary working up" means: if necessary, water is added, the mixture is adjusted, if necessary, depending on the constitution of the final product, to a pH of between 2 and 10 and extracted with ethyl acetate or dichloromethane, the organic phase is separated off, dried over sodium sulfate and evaporated, and the residue is purified by chromatography on silica gel, whereupon a separation of the isomers described below also takes place, and/or by crystallization, $Rf_A$ values on silica gel, eluent: ethyl acetate/methanol 9:1; $Rf_B$ values on silica gel, eluent toluene/methyl tert-butyl ether 1:1; $Rf_C$ values on silica gel, eluent petroleum ether/ethyl acetate 4:1; $Rf_D$ values on silica gel, eluent methyl tert-butyl ether/petroleum ether 1:1.

Example 1

A 50% solution of 1.8 g of 2-methoxybenzyl chloride ("A") in dichloromethane is added to a solution of 2.0 g of ethyl 4-(1,4-benzodioxan-6-yl)-1,2-dihydro-2-oxobenzofuro[3,2-b]pyridine-3-carboxylate (obtainable by reaction of 3-amino-2-(1,4-benzodioxan-6-carbonyl) benzofuran and diethyl malonate in acetone and potassium carbonate, m.p. 255°; 3-amino-2-(1,4-benzodioxan-6-carbonyl)benzofuran is obtainable by reaction of 2-hydroxybenzonitrile and 6-bromoacetyl-1,4-benzodioxane, m.p. 157°) in 15 ml of DMF and 2.5 g of caesium carbonate. The reaction mixture is stirred for 10 hours and worked up in the customary manner. The N-alkylation product ethyl 4-(1,4-benzodioxan-6-yl)-1,2-dihydro-1-(2-methoxybenzyl)-2-oxobenzofuro[3,2-b]pyridine-3-carboxylate, m.p. 105° and the O-alkylation product ethyl 4-(1,4-benzodioxan-6-yl)-2-(2-methoxybenzyloxy)benzofuro[3,2-b]pyridine-3-carboxylate, m.p. 166°, are obtained.

Analogously, starting from the following ethyl 4-T-1,2-dihydro-2-oxobenzofuro[3,2-b]pyridine-3-carboxylates in which T is phenyl, m.p. 291°
naphthyl
1,4-benzodioxan-5-yl
1,3-benzodioxol-4-yl
1,3-benzodioxol-5-yl, m.p. 246°
2-methoxyphenyl, m.p. 192°
3-methoxyphenyl, m.p. 186°
4-methoxyphenyl, m.p. 247°
2,3-dimethoxyphenyl
2,4-dimethoxyphenyl, m.p. 220°
2,5-dimethoxyphenyl, m.p. 217°
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl, m.p. 208°
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl, m.p. 208°
4-trifluoromethoxy-2-carboxymethyloxyphenyl
3,4,5-trimethoxyphenyl, m.p. 166°
4-ethoxyphenyl, m.p. 223°
4-diethylaminophenyl, m.p. 244°
4-methylthiophenyl, m.p. 228°
3-fluoro-4-methoxyphenyl, m.p. 266°
2,3-dihydro-5-benzofuryl, m.p. 268°
4-methylphenyl, m.p. 246°
2-ethoxy-5-methoxyphenyl, m.p.>300°
2,1,3-benzothiadiazol-5-yl
2,4,5-trimethoxyphenyl
3-chloro-4-methoxyphenyl
2-fluoro-4-methoxyphenyl with "A" the ethyl 4-T-1,2-dihydro-1-(2-methoxybenzyl)-2-oxobenzofuro[3,2-b]pyridine-3-carboxylates below are obtained, in which T is phenyl
naphthyl
1,4-benzodioxan-5-yl
1,3-benzodioxol-4-yl
1,3-benzodioxol-5-yl, $Rf_B$ 0.55
2-methoxyphenyl, $Rf_C$ 0.39
3-methoxyphenyl, $Rf_B$ 0.51
4-methoxyphenyl, m.p. 109°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl, m.p. 222°
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl 2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl, $Rf_B$ 0.50
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl, $Rf_C$ 0.37
2,3-dihydro-5-benzofuryl, $Rf_C$ 0.36
4-methylphenyl
2-ethoxy-5-methoxyphenyl, $Rf_C$ 0.41
2,1,3-benzothiadiazol-5-yl
2,4,5-trimethoxyphenyl
3-chloro-4-methoxyphenyl
2-fluoro-4-methoxyphenyl
and also the ethyl 4-T-2-(2-methoxybenzyloxy)benzofuro[3, 2-b]pyridine-3-carboxylates below, in which T is
phenyl
naphthyl
1,4-benzodioxan-5-yl
1,3-benzodioxol-4-yl
1,3-benzodioxol-5-yl, m.p. 146°
2-methoxyphenyl, m.p. 181°
3-methoxyphenyl, m.p. 108°
4-methoxyphenyl, m.p. 141°
2,3-dimethoxyphenyl
2,4-dimethoxyphenyl, $Rf_D$ 0.75
2,5-dimethoxyphenyl, m.p. 121°
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl, m.p. 100°
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl, m.p. 180°
4-trifluoromethoxy-2-carboxymethyloxyphenyl
3,4,5-trimethoxyphenyl
4-ethoxyphenyl
4-diethylaminophenyl, m.p. 102°
4-methylthiophenyl, m.p. 188°
3-fluoro-4-methoxyphenyl, m.p. 176°
2,3-dihydro-5-benzofuryl, m.p. 140°
4-methylphenyl, m.p. 126°
2-ethoxy-5-methoxyphenyl, m.p. 109°
2,1,3-benzothiadiazol-5-yl
2,4,5-trimethoxyphenyl
3-chloro-4-methoxyphenyl
2-fluoro-4-methoxyphenyl.

Analogously, by reaction of 3-methoxybenzyl chloride with the following ethyl 4-T-1,2-dihydro-2-oxobenzofuro[3, 2-b]pyridine-3-carboxylates, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 247°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
the ethyl 4-T-1,2-dihydro-1-(3-methoxybenzyl)-2-oxo-benzofuro[3,2-b]pyridine-3-carboxylates below are obtained, in which T is
phenyl naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 104°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
and also the ethyl 4-T-2-(3-methoxybenzyloxy)benzofuro[3,2-b]pyridine-3-carboxylates below, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 106°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl.

Analogously, by reaction of 4-methoxybenzyl chloride with the following ethyl 4-T-1,2-dihydro-2-oxobenzofuro[3,2-b]pyridine-3-carboxylates, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 247°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl 2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, the ethyl 4-T-1,2-dihydro-1-(4-methoxybenzyl)-2-oxobenzofuro[3,2-b]pyridine-3-carboxylates below are obtained, in which T is phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 192°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, and also the ethyl 4-T-2-(4-methoxybenzyloxy)benzofuro[3,2-b]pyridine-3-carboxylates below, in which T is phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 108°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl 2-fluoro-4-methoxyphenyl.

Analogously, by reaction of 3,4-methylenedioxybenzyl chloride with the following ethyl 4-T-1,2-dihydro-2-oxobenzofuro[3,2-b]pyridine-3-carboxylates, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 247°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
the ethyl 4-T-1,2-dihydro-1-(3,4-methylenedioxybenzyl)-2-oxobenzofuro[3,2-b]pyridine-3-carboxylates below are obtained, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 177°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
and also the ethyl 4-T-2-(3,4-methylenedioxybenzyloxy) benzofuro[3,2-b]pyridine-3-carboxylates below, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 124°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl 4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl.

Analogously, by reaction of 2-carboxymethyloxy-4-methoxybenzyl chloride with the following ethyl 4-T-1,2-dihydro-2-oxobenzofuro[3,2-b]pyridine-3-carboxylates, in which T is
phenyl
naphthyl
1,4-benzodioxan-6-yl
1,4-benzodioxano5-yl
1,3-benzodioxol-4-yl
1,3-benzodioxol-5-yl
2-methoxyphenyl
3-methoxyphenyl
4-methoxyphenyl, m.p. 247°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, the ethyl 4-T-1,2-dihydro-1-(2-carboxymethyloxy-4-methoxybenzyl)-2-oxobenzofuro[3,2-b]pyridine-3-carboxylates below are obtained, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl 4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, and also the ethyl 4-T-2-(2-carboxymethyloxy-4-methoxybenzyloxy)benzofuro[3,2-b]pyridine-3-carboxylates below, in which T is phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 102°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl.

Analogously, by reaction of 2,3-methylenedioxybenzyl chloride with the following ethyl 4-T-1,2-dihydro-2-oxobenzofuro[3,2-b]pyridine-3-carboxylates, in which T is phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 247°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, the ethyl 4-T-1,2-dihydro-1-(2,3-methylenedioxybenzyl)-2-oxobenzofuro[3,2-b]pyridine-3-carboxylates below are obtained, in which T is phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, $Rf_C$ 0.41
2,3-dimethoxyphenyl 2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
and also the ethyl 4-T-2-(2,3-methylenedioxybenzyloxy)benzofuro[3,2-b]pyridine-3-carboxylates below, in which T is
    phenyl
    naphthyl
    1,4-benzodioxan-6-yl
    1,4-benzodioxan-5-yl
    1,3-benzodioxol-4-yl
    1,3-benzodioxol-5-yl
    2-methoxyphenyl
    3-methoxyphenyl
    4-methoxyphenyl, m.p. 184°
    2,3-dimethoxyphenyl
    2,4-dimethoxyphenyl
    2,5-dimethoxyphenyl
    3,4-dimethoxyphenyl
    3,5-dimethoxyphenyl
    2-carboxymethyloxyphenyl
    3-carboxymethyloxyphenyl
    4-carboxymethyloxyphenyl
    2-difluoromethoxyphenyl
    3-difluoromethoxyphenyl
    4-difluoromethoxyphenyl
    2-methoxy-3-carboxymethyloxyphenyl
    2-methoxy-4-carboxymethyloxyphenyl
    2-carboxymethyloxy-3-methoxyphenyl
    2-carboxymethyloxy-4-methoxyphenyl
    2-difluoromethoxy-3-carboxymethyloxyphenyl
    2-difluoromethoxy-4-carboxymethyloxyphenyl
    2-carboxymethyloxy-3-difluoromethoxyphenyl
    2-carboxymethyloxy-4-difluoromethoxyphenyl
    2-trifluoromethoxyphenyl
    3-trifluoromethoxyphenyl
    4-trifluoromethoxyphenyl
    4-trifluoromethoxy-2-carboxymethyloxyphenyl
    3,4,5-trimethoxyphenyl
    4-ethoxyphenyl
    4-diethylaminophenyl
    4-methylthiophenyl
    3-fluoro-4-methoxyphenyl
    2,3-dihydro-5-benzofuryl
    4-methylphenyl
    2-ethoxy-5-methoxyphenyl
    2,1,3-benzothiadiazol-5-yl
    2,4,5-trimethoxyphenyl
    3-chloro-4-methoxyphenyl
    2-fluoro-4-methoxyphenyl.

Analogously, by reaction of 2-methylthiobenzyl chloride with the following ethyl 4-T-1,2-dihydro-2-oxobenzofuro[3,2-b]pyridine-3-carboxylates, in which T is
    phenyl
    naphthyl
    1,4-benzodioxan-6-yl
    1,4-benzodioxan-5-yl
    1,3-benzodioxol-4-yl
    1,3-benzodioxol-5-yl
    2-methoxyphenyl
    3-methoxyphenyl
    4-methoxyphenyl, m.p. 247°
    2,3-dimethoxyphenyl
    2,4-dimethoxyphenyl
    2,5-dimethoxyphenyl
    3,4-dimethoxyphenyl
    3,5-dimethoxyphenyl
    2-carboxymethyloxyphenyl
    3-carboxymethyloxyphenyl
    4-carboxymethyloxyphenyl
    2-difluoromethoxyphenyl
    3-difluoromethoxyphenyl
    4-difluoromethoxyphenyl
    2-methoxy-3-carboxymethyloxyphenyl
    2-methoxy-4-carboxymethyloxyphenyl
    2-carboxymethyloxy-3-methoxyphenyl
    2-carboxymethyloxy-4-methoxyphenyl
    2-difluoromethoxy-3-carboxymethyloxyphenyl
    2-difluoromethoxy-4-carboxymethyloxyphenyl
    2-carboxymethyloxy-3-difluoromethoxyphenyl
    2-carboxymethyloxy-4-difluoromethoxyphenyl
    2-trifluoromethoxyphenyl
    3-trifluoromethoxyphenyl 4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
the ethyl 4-T-1,2-dihydro-1-(2-methylthiobenzyl)-2-oxobenzofuro[3,2-b]pyridine-3-carboxylates below are obtained, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, $Rf_C$ 0.3
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
and also the ethyl 4-T-2-(2-methylthiobenzyloxy)benzofuro[3,2-b]pyridine-3-carboxylates below, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 122°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl.

Analogously, by reaction of 2,3-dimethoxybenzyl chloride with the following ethyl 4-T-1,2-dihydro-2-oxobenzofuro[3,2-b]pyridine-3-carboxylates, in which T is
phenyl
naphthyl
1,4-benzodioxan-6-yl
1,4-benzodioxan-5-yl 1,3-benzodioxol-4-yl
1,3-benzodioxol-5-yl
2-methoxyphenyl
3-methoxyphenyl
4-methoxyphenyl, m.p. 247°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
the ethyl 4-T-1,2-dihydro-1-(2,3-dimethoxybenzyl)-2-oxobenzofuro[3,2-b]pyridine-3-carboxylates below are obtained, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 166°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
and also the ethyl 4-T-2-(2,3-dimethoxybenzyloxy)benzofuro[3,2-b]pyridine-3-carboxylates below, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 121°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl 2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl.

Analogously, by reaction of 2,5-dimethoxybenzyl chloride with the following ethyl 4-T-1,2-dihydro-2-oxobenzofuro[3,2-b]pyridine-3-carboxylates, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 247°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, the ethyl 4-T-1,2-dihydro-1-(2,5-dimethoxybenzyl)-2-oxobenzofuro[3,2-b]pyridine-3-carboxylates below are obtained, in which T is
phenyl
naphthyl
1,4-benzodioxan-6-yl
1,4-benzodioxan-5-yl
1,3-benzodioxol-4-yl
1,3-benzodioxol-5-yl, $Rf_c$ 0.42
2-methoxyphenyl
3-methoxyphenyl
4-methoxyphenyl, $Rf_c$ 0.37
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl, $Rf_c$ 0.35
4-diethylaminophenyl
4-methylthiophenyl
3-fluoro-4-methoxyphenyl, m.p. 155°
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, and also the ethyl 4-T-2-(2,5-dimethoxybenzyloxy) benzofuro[3,2-b]pyridine-3-carboxylates below, in which T is phenyl
naphthyl
1,4-benzodioxano6-yl
1,4-benzodioxano5-yl
1,3-benzodioxol-4-yl
1,3-benzodioxol-5-yl, m.p. 145°
2-methoxyphenyl
3-methoxyphenyl
4-methoxyphenyl, m.p. 114°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl, m.p. 96°
4-diethylaminophenyl
4-methylthiophenyl
3-fluoro-4-methoxyphenyl, m.p. 136°
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl.

Analogously, by reaction of 2,1,3-benzothiadiazole-5-methyl chloride with the following ethyl 4-T-1,2-dihydro-2-oxobenzofuro[3,2-b]pyridine-3-carboxylates, in which T is phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 247°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, the ethyl 4-T-1,2-dihydro-1-(2,1,3-benzothiazole-5-methyl)-2-oxobenzofuro[3,2-b]pyridine-3-carboxylates below are obtained, in which T is phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 221°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl 4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
and also the ethyl 4-T-2-(2,1,3-benzothiadiazole-5-methyloxy)benzofuro[3,2-b]pyridine-3-carboxylates below, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 183°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl.

Analogously, by reaction of 3,4-methylenedioxy-6-chlorobenzyl chloride with the following ethyl 4-T-2-dihydro-2-oxobenzofuro[3,2-b]pyridine-3-carboxylates, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 247°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl 4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, the ethyl 4-T-1,2-dihydro-1-(3,4-methylenedioxy-6-chlorobenzyl)-2-oxobenzofuro[3,2-b]pyridine-3-carboxylates below are obtained, in which T is phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, $Rf_D$ 0.67
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, and also the ethyl 4-T-2-(3,4-methylenedioxy-6-chlorobenzyloxy)benzofuro[3,2-b]pyridine-3-carboxylates below, in which T is phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl, m.p. 167°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl.

Analogously, by reaction of 2-methoxybenzyl chloride with the following ethyl 4-T-1,2-dihydro-2-oxo-7-methyl-benzofuro[3,2-b]pyridine-3-carboxylates, in which T is phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl
2,3-dimethoxyphenyl 2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
the ethyl 4-T-1,2-dihydro-1-(2-methoxybenzyl)-2-oxo-7-methylbenzofuro[3,2-b]pyridine-3-carboxylates below are obtained, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
and also the ethyl 4-T-2-(2-methoxybenzyloxy)-7-methylbenzofuro[3,2-b]pyridine-3-carboxylates below, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl 4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl.

Analogously, by reaction of 2-methoxybenzyl chloride with the following ethyl 4-T-1,2-dihydro-2-oxobenzothieno[3,2-b]pyridine-3-carboxylates, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, the ethyl 4-T-1,2-dihydro-1-(2-methoxybenzyl)-2-oxobenzothieno[3,2-b]pyridine-3-carboxylates below are obtained, in which T is
phenyl
naphthyl
1,4-benzodioxan-6-yl
1,4-benzodioxan-5-yl
1,3-benzodioxol-4-yl
1,3-benzodioxol-5-yl
2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, and also the ethyl 4-T-2-(2-methoxybenzyloxy)benzothieno[3,2-b]pyridine-3-carboxylates below, in which T is
phenyl
naphthyl
1,4-benzodioxan-6-yl
1,4-benzodioxan-5-yl 1,3-benzodioxol-4-yl
1,3-benzodioxol-5-yl
2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl.

Example 2

A solution of 0.5 g of ethyl 4-(1,4-benzodioxan-6-yl)-1,2-dihydro-1-(2-methoxybenzyl)-2-oxo-benzofuro[3,2-b]pyridine-3-carboxylate and 6 ml of 5N KOH in 10 ml of methanol is boiled under reflux for 2 hours. The mixture is worked up in the customary manner and 4-(1,4-benzodioxan-6-yl)-1,2-dihydro-1-(2-methoxybenzyl)-2-oxo-benzofuro[3,2-b]pyridine-3-carboxylic acid, m.p. 225°, is obtained.

Analogously, starting from ethyl 4-(1,4-benzodioxan-6-yl)-2-(2-methoxybenzyloxy)benzofuro[3,2-b]pyridine-3-carboxylate, the O-alkylation product 4-(1,4-benzodioxan-6-yl)-2-(2-methoxybenzyloxy)benzofuro[3,2-b]pyridine-3-carboxylic acid, m.p. 179°, is obtained.

Analogously, starting from the
ethyl 4-T-1,2-dihydro-1-(2-methoxybenzyl)-2-oxobenzofuro[3,2-b]pyridine-3-carboxylates,
ethyl 4-T-2-(2-methoxybenzyloxy)benzofuro[3,2-b]pyridine-3-carboxylates,
ethyl 4-T-1,2-dihydro-1-(3-methoxybenzyl)-2-oxobenzofuro[3,2-b]pyridine-3-carboxylates,
ethyl 4-T-2-(3-methoxybenzyloxy)benzofuro[3,2-b]pyridine-3-carboxylates,
ethyl 4-T-1,2-dihydro-1-(4-methoxybenzyl)-2-oxobenzofuro[3,2-b]pyridine-3-carboxylates,
ethyl 4-T-2-(4-methoxybenzyloxy)benzofuro[3,2-b]pyridine-3-carboxylates,
ethyl 4-T-1,2-dihydro-1-(3,4-methylenedioxybenzyl)-2-oxobenzofuro[3,2-b]pyridine-3-carboxylates,
ethyl 4-T-2-(3,4-methylenedioxybenzyloxy)-benzofuro[3,2-b]pyridine-3-carboxylates,
ethyl 4-T-1,2-dihydro-1-(2-carboxymethyloxy-4-methoxybenzyl)-2-oxobenzofuro[3,2-b]pyridine-3-carboxylates,
ethyl 4-T-2-(2-carboxymethyloxy-4-methoxybenzyloxy)benzofuro[3,2-b]pyridine-3-carboxylates,
ethyl 4-T-1,2-dihydro-1-(2,3-methylenedioxybenzyl)-2-oxobenzofuro[3,2-b]pyridine-3-carboxylates,
ethyl 4-T-2-(2,3-methylenedioxybenzyloxy)benzofuro[3,2-b]pyridine-3-carboxylates,
ethyl 4-T-1,2-dihydro-1-(2-methylthiobenzyl)-2-oxobenzofuro[3,2-b]-pyridine-3-carboxylates,
ethyl 4-T-2-(2-methylthiobenzyloxy)benzofuro[3,2-b]-pyridine-3-carboxylates,
ethyl 4-T-1,2-dihydro-1-(2,3-dimethoxybenzyl)-2-oxobenzofuro[3,2-b]pyridine-3-carboxylates,
ethyl 4-T-2-(2,3-dimethoxybenzyloxy)benzofuro[3,2-b]-pyridine-3-carboxylates,
ethyl 4-T-1,2-dihydro-1-(2,5-dimethoxybenzyl)-2-oxobenzofuro[3,2-b]pyridine-3-carboxylates,
ethyl 4-T-2-(2,5-dimethoxybenzyloxy)benzofuro[3,2-b]-pyridine-3-carboxylates,
ethyl 4-T-1,2-dihydro-1-(2,1,3-benzothiazole-5-methyl)-2-oxobenzofuro[3,2-b]pyridine-3-carboxylates,
ethyl 4-T-2-(2,1,3-benzothiadiazole-5-methyloxy)benzofuro[3,2-b]pyridine-3-carboxylates,
ethyl 4-T-1,2-dihydro-1-(3,4-methylenedioxy-6-chlorobenzyl)-2-oxobenzofuro[3,2-b]pyridine-3-carboxylates,
ethyl 4-T-2-(3,4-methylenedioxy-6-chlorobenzyloxy)benzofuro[3,2-b]pyridine-3-carboxylates,
ethyl 4-T-1,2-dihydro-1-(2-methoxybenzyl)-2-oxo-7-methylbenzofuro[3,2-b]pyridine-3-carboxylates,
ethyl 4-T-2-(2-methoxybenzyloxy)-7-methylbenzofuro[3,2-b]-pyridine-3-carboxylates,
ethyl 4-T-1,2-dihydro-1-(2-methoxybenzyl)-2-oxobenzothieno[3,2-b]pyridine-3-carboxylates and
ethyl 4-T-2-(2-methoxybenzyloxy)benzothieno[3,2-b]-pyridine-3-carboxylates below
in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl
2,3-dimethoxyphenyl
2,4-dimethoxyphenyl 2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
the following
4-T-1,2-dihydro-1-(2-methoxybenzyl)-2-oxobenzofuro[3,2-b]pyridine-3-carboxylic acids, in which T is
phenyl
naphthyl
1,4-benzodioxan-5-yl
1,3-benzodioxol-4-yl
1,3-benzodioxol-5-yl, m.p. 230°
2-methoxyphenyl, m.p. 228°
3-methoxyphenyl, potassium salt, m.p.>300°
4-methoxyphenyl, potassium salt, m.p. 258°
2,3-dimethoxyphenyl
2,4-dimethoxyphenyl, m.p. 266°
2,5-dimethoxyphenyl, m.p. 201°
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl, m.p. 214°
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl, m.p. 193°
4-trifluoromethoxy-2-carboxymethyloxyphenyl
3,4,5-trimethoxyphenyl
4-ethoxyphenyl
4-diethylaminophenyl, m.p. 195°
4-methylthiophenyl, m.p. 240°
3-fluoro-4-methoxyphenyl, m.p. 254°
2,3-dihydro-5-benzofuryl, m.p. 267°
4-methylphenyl, m.p. 243°
2-ethoxy-5-methoxyphenyl, m.p. 245°
2,1,3-benzothiadiazol-5-yl
2,4,5-trimethoxyphenyl
3-chloro-4-methoxyphenyl
2-fluoro-4-methoxyphenyl,
4T-2-(2-methoxybenzyloxy)benzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, m.p. 105°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl 4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-1,2-dihydro-1-(3-methoxybenzyl)-2-oxobenzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, m.p. 223°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-2-(3-methoxybenzyloxy)benzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, m.p. 174°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-1,2-dihydro-1-(4-methoxybenzyl)-2-oxobenzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, m.p. 244°
2,3-dimethoxyphenyl
2,4-dimethoxyphenyl
2,5-dimethoxyphenyl
3,4-dimethoxyphenyl 3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, 4-T-2-(4-methoxybenzyloxy)benzofuro[3,2-b]pyridine-3-carboxylic acids, in which T is phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, m.p. 232°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, 4-T-1,2-dihydro-1-(3,4-methylenedioxybenzyl)-2-oxobenzofuro[3,2-b]pyridine-3-carboxylic acids, in which T is phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, potassium salt, m.p.>300°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl 3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-2-(3,4-methylenedioxybenzyloxy)benzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, m.p. 89°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-1,2-dihydro-1-(2-carboxymethyloxy-4-methoxybenzyl)-2-oxobenzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-2-(2-carboxymethyloxy-4-methoxybenzyloxy)benzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, m.p. 217°
2,3-dimethoxyphenyl
2,4-dimethoxyphenyl
2,5-dimethoxyphenyl
3,4-dimethoxyphenyl
3,5-dimethoxyphenyl 2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, 4-T-1,2-dihydro-1-(2,3-methylenedioxybenzyl)-2-oxobenzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, m.p. 214°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl, 4-T-2-(2,3-methylenedioxybenzyloxy)benzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl 2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-1,2-dihydro-1-(2-methylthiobenzyl)-2-oxobenzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, m.p.>300°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-2-(2-methylthiobenzyloxy)benzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-1,2-dihydro-1-(2,3-dimethoxybenzyl)-2-oxobenzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, m.p. 251°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl 4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-2-(2,3-dimethoxybenzyloxy)benzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl 2-trifluoromethoxyphenyl
3-trifluoromethoxyphenyl
4-trifluoromethoxyphenyl
4-trifluoromethoxy-2-carboxymethyloxyphenyl,
4-T-1,2-dihydro-1-(2,5-dimethoxybenzyl)-2-oxobenzofuro[3,2-b]pyridine-3-carboxylic acids, in which T is
phenyl
naphthyl
1,4-benzodioxan-5-yl
1,3-benzodioxol-4-yl
1,3-benzodioxol-5-yl, m.p. 263°
2-methoxyphenyl
3-methoxyphenyl
4-methoxyphenyl, m.p. 297°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl, m.p. 197°
4-diethylaminophenyl
4-methylthiophenyl
3-fluoro-4-methoxyphenyl, potassium salt, m.p. 283°
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-2-(2,5-dimethoxybenzyloxy)benzofuro[3,2-b]pyridine-3-carboxylic acids, in which T is
phenyl
naphthyl
1,4-benzodioxan-5-yl
1,3-benzodioxol-4-yl
1,3-benzodioxol-5-yl 2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-1,2-dihydro-1-(2,1,3-benzothiazole-5-methyl)-2-oxobenzofuro[3,2-b]pyridine-3-carboxylic acids, in which T is
 phenyl
 naphthyl
 1,4-benzodioxan-5-yl
 1,3-benzodioxol-4-yl
 1,3-benzodioxol-5-yl
 2-methoxyphenyl
 3-methoxyphenyl
 4-methoxyphenyl, m.p. 114°
 2,3-dimethoxyphenyl
 2,4-dimethoxyphenyl
 2,5-dimethoxyphenyl
 3,4-dimethoxyphenyl
 3,5-dimethoxyphenyl
 2-carboxymethyloxyphenyl
 3-carboxymethyloxyphenyl
 4-carboxymethyloxyphenyl
 2-difluoromethoxyphenyl
 3-difluoromethoxyphenyl
 4-difluoromethoxyphenyl
 2-methoxy-3-carboxymethyloxyphenyl
 2-methoxy-4-carboxymethyloxyphenyl
 2-carboxymethyloxy-3-methoxyphenyl
 2-carboxymethyloxy-4-methoxyphenyl
 2-difluoromethoxy-3-carboxymethyloxyphenyl
 2-difluoromethoxy-4-carboxymethyloxyphenyl
 2-carboxymethyloxy-3-difluoromethoxyphenyl
 2-carboxymethyloxy-4-difluoromethoxyphenyl
 2-trifluoromethoxyphenyl
 3-trifluoromethoxyphenyl
 4-trifluoromethoxyphenyl
 4-trifluoromethoxy-2-carboxymethyloxyphenyl
 3,4,5-trimethoxyphenyl
 4-ethoxyphenyl
 4-diethylaminophenyl
 4-methylthiophenyl
 3-fluoro-4-methoxyphenyl
 2,3-dihydro-5-benzofuryl
 4-methylphenyl
 2-ethoxy-5-methoxyphenyl
 2,1,3-benzothiadiazol-5-yl
 2,4,5-trimethoxyphenyl
 3-chloro-4-methoxyphenyl
 2-fluoro-4-methoxyphenyl,
4-T-2-(2,1,3-benzothiadiazole-5-methyloxy)benzofuro[3,2-b]pyridine-3-carboxylic acids, in which T is
 phenyl
 naphthyl
 1,4-benzodioxan-5-yl
 1,3-benzodioxol-4-yl
 1,3-benzodioxol-5-yl
 2-methoxyphenyl
 3-methoxyphenyl
 4-methoxyphenyl
 2,3-dimethoxyphenyl
 2,4-dimethoxyphenyl
 2,5-dimethoxyphenyl
 3,4-dimethoxyphenyl
 3,5-dimethoxyphenyl
 2-carboxymethyloxyphenyl
 3-carboxymethyloxyphenyl
 4-carboxymethyloxyphenyl
 2-difluoromethoxyphenyl
 3-difluoromethoxyphenyl
 4-difluoromethoxyphenyl
 2-methoxy-3-carboxymethyloxyphenyl
 2-methoxy-4-carboxymethyloxyphenyl
 2-carboxymethyloxy-3-methoxyphenyl
 2-carboxymethyloxy-4-methoxyphenyl
 2-difluoromethoxy-3-carboxymethyloxyphenyl
 2-difluoromethoxy-4-carboxymethyloxyphenyl
 2-carboxymethyloxy-3-difluoromethoxyphenyl
 2-carboxymethyloxy-4-difluoromethoxyphenyl
 2-trifluoromethoxyphenyl 3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-1,2-dihydro-1-(3,4-methylenedioxy-6-chlorobenzyl)-2-oxobenzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, potassium salt, m.p.>300°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-b-4-methoxyphenyl,
4-T-2-(3,4-methylenedioxy-6-chlorobenzyloxy)benzofuro[3,2-b]pyridine-3-carboxylic acids, in which T is
phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl, m.p. 192°
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4- ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-1,2-dihydro-1-(2-methoxybenzyl)-2-oxo-7-methylbenzofuro[3,2-b]pyridine-3-carboxylic acids, in which T is
phenyl
naphthyl
1,4-benzodioxan-5-yl
1,3-benzodioxol-4-yl
1,3-benzodioxol-5-yl 2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
4-T-2-(2-methoxybenzyloxy)-7-methylbenzofuro[3,2-b]
pyridine-3-carboxylic acids, in which T
 phenyl
 naphthyl
 1,4-benzodioxan-5-yl
 1,3-benzodioxol-4-yl
 1,3-benzodioxol-5-yl
 2-methoxyphenyl
 3-methoxyphenyl
 4-methoxyphenyl
 2,3-dimethoxyphenyl
 2,4-dimethoxyphenyl
 2,5-dimethoxyphenyl
 3,4-dimethoxyphenyl
 3,5-dimethoxyphenyl
 2-carboxymethyloxyphenyl
 3-carboxymethyloxyphenyl
 4-carboxymethyloxyphenyl-2-difluoromethoxyphenyl
 3-difluoromethoxyphenyl
 4-difluoromethoxyphenyl
 2-methoxy-3-carboxymethyloxyphenyl
 2-methoxy-4-carboxymethyloxyphenyl
 2-carboxymethyloxy-3-methoxyphenyl
 2-carboxymethyloxy-4-methoxyphenyl
 2-difluoromethoxy-3-carboxymethyloxyphenyl
 2-difluoromethoxy-4-carboxymethyloxyphenyl
 2-carboxymethyloxy-3-difluoromethoxyphenyl
 2-carboxymethyloxy-4-difluoromethoxyphenyl
 2-trifluoromethoxyphenyl
 3-trifluoromethoxyphenyl
 4-trifluoromethoxyphenyl
 4-trifluoromethoxy-2-carboxymethyloxyphenyl
 3,4,5-trimethoxyphenyl
 4-ethoxyphenyl
 4-diethylaminophenyl
 4-methylthiophenyl
 3-fluoro-4-methoxyphenyl
 2,3-dihydro-5-benzofuryl
 4-methylphenyl
 2-ethoxy-5-methoxyphenyl
 2,1,3-benzothiadiazol-5-yl
 2,4,5-trimethoxyphenyl
 3-chloro-4-methoxyphenyl
 2-fluoro-4-methoxyphenyl,
4-T-1,2-dihydro-1-(2-methoxybenzyl)-2-oxobenzothieno[3,2-b]pyridine-3-carboxylic acids, in which T is
 phenyl
 naphthyl
 1,4-benzodioxan-5-yl
 1,3-benzodioxol-4-yl
 1,3-benzodioxol-5-yl
 2-methoxyphenyl
 3-methoxyphenyl
 4-methoxyphenyl
 2,3-dimethoxyphenyl
 2,4-dimethoxyphenyl
 2,5-dimethoxyphenyl
 3,4-dimethoxyphenyl
 3,5-dimethoxyphenyl
 2-carboxymethyloxyphenyl
 3-carboxymethyloxyphenyl
 4-carboxymethyloxyphenyl
 2-difluoromethoxyphenyl
 3-difluoromethoxyphenyl
 4-difluoromethoxyphenyl
 2-methoxy-3-carboxymethyloxyphenyl
 2-methoxy-4-carboxymethyloxyphenyl
 2-carboxymethyloxy-3-methoxyphenyl
 2-carboxymethyloxy-4-methoxyphenyl
 2-difluoromethoxy-3-carboxymethyloxyphenyl
 2-difluoromethoxy-4-carboxymethyloxyphenyl
 2-carboxymethyloxy-3-difluoromethoxyphenyl
 2-carboxymethyloxy-4-difluoromethoxyphenyl
 2-trifluoromethoxyphenyl
 3-trifluoromethoxyphenyl
 4-trifluoromethoxyphenyl 4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
and
4-T-2-(2-methoxybenzyloxy)benzothieno[3,2-b]pyridine-3-carboxylic acids, in which T is phenyl
naphthyl
1,4-benzodioxan-5-yl
1,3-benzodioxol-4-yl
1,3-benzodioxol-5-yl
2-methoxyphenyl
3-methoxyphenyl
4-methoxyphenyl
2,3-dimethoxyphenyl
2,4-dimethoxyphenyl
2,5-dimethoxyphenyl
3,4-dimethoxyphenyl
3,5-dimethoxyphenyl
2-carboxymethyloxyphenyl
3-carboxymethyloxyphenyl
4-carboxymethyloxyphenyl
2-difluoromethoxyphenyl
3-difluoromethoxyphenyl
4-difluoromethoxyphenyl
2-methoxy-3-carboxymethyloxyphenyl
2-methoxy-4-carboxymethyloxyphenyl
2-carboxymethyloxy-3-methoxyphenyl
2-carboxymethyloxy-4-methoxyphenyl
2-difluoromethoxy-3-carboxymethyloxyphenyl
2-difluoromethoxy-4-carboxymethyloxyphenyl
2-carboxymethyloxy-3-difluoromethoxyphenyl
2-carboxymethyloxy-4-difluoromethoxyphenyl
2-trifluoromethoxyphenyl
3-trifluoromethoxyphenyl
4-trifluoromethoxyphenyl
4-trifluoromethoxy-2-carboxymethyloxyphenyl
3,4,5-trimethoxyphenyl
4-ethoxyphenyl
4-diethylaminophenyl
4-methylthiophenyl
3-fluoro-4-methoxyphenyl
2,3-dihydro-5-benzofuryl
4-methylphenyl
2-ethoxy-5-methoxyphenyl
2,1,3-benzothiadiazol-5-yl
2,4,5-trimethoxyphenyl
3-chloro-4-methoxyphenyl
2-fluoro-4-methoxyphenyl,
are obtained.

Example 3

A solution of 4.1 g of ethyl 4-(1,4-benzodioxan-6-yl)-2-chlorobenzofuro[3,2-b]pyridine-3-carboxylate and 0.25 g of tetrakis(triphenylphosphine)palladium(0) in 50 ml of toluene is treated with 10 ml of a 2M aqueous sodium carbonate solution and 1.52 g of 4-methoxyphenylboronic acid in 25 ml of methanol and boiled under reflux for 1 hour under an inert gas atmosphere.

The mixture is worked up in the customary manner and ethyl 4-(1,4-benzodioxan-6-yl)-2-(4-methoxyphenyl)benzofuro[3,2-b]pyridine-3-carboxylate is obtained.

Example 4

A solution of 3.8 g of ethyl 4-(1,4-benzodioxan-6-yl)-2-chlorobenzofuro[3,2-b]pyridine-3-carboxylate and 3.1 g of caesium carbonate in 40 ml of DMF is treated with a solution of 1.7 g of 3,4-methylenedioxyphenol in 20 ml of dichloromethane and stirred overnight. The mixture is worked up in the customary manner and ethyl 4-(1,4-benzodioxan-6-yl)-2-(3,4-methylenedioxyphenoxy)benzofuro[3,2-b]pyridine-3-carboxylate is obtained.

Example 5

A solution of 1 g of 1,2-dihydro-1-(2-methoxybenzyl)-4-(4-methoxyphenyl)-2-oxo-7-nitrobenzofuro[3,2-b]pyridine-3-carboxylic acid, m.p. 245°, prepared analogously to Examples 1 and 2, in 25 ml of methanol is hydrogenated to completion on 1 g of Raney nickel at normal pressure and 20°. The mixture is filtered, the solvent is removed and 7-amino-1,2-dihydro-1-(2-methoxybenzyl)-4-(4-methoxyphenyl)-2-oxobenzofuro[3,2-b]pyridine-3-carboxylic acid, m.p. 268°, is obtained.

Example 6

A solution of 6 g of 7-amino-1,2-dihydro-1-(2-methoxybenzyl)-4-(4-methoxyphenyl)-2-oxobenzofuro-[3,2-b]pyridine-3-carboxylic acid and 0.5 g of titanium tetrachloride in 100 ml of methanol is treated with 1 ml of freshly distilled acetaldehyde. 4 g of sodium cyanoborohydride are then added and the mixture is stirred for 30 hours. Half-concentrated hydrochloric acid is added, the mixture is worked up in the customary manner and 7-ethylamino-1,2-dihydro-1-(2-methoxybenzyl)-4-(4-methoxyphenyl)-2-oxobenzofuro-[3,2-b]pyridine-3-carboxylic acid is obtained.

Example 7

A solution of 4.85 g of 4-(1,4-benzodioxan-6-yl)-1,2-dihydro-1-(3,4-methylenedioxybenzyl)-2-oxobenzofuro-[3,2-b]pyridine-3-carboxylic acid and 0.2 g of dimethylaminopyridine in 50 ml of pyridine is treated with 5 ml of thionyl chloride and 1.57 g of phenylsulfonamide. The mixture is stirred for 10 hours and worked up in the customary manner, and 4-(1,4-benzodioxan-6-yl)-1,2-dihydro-1-(3,4-methylenedioxybenzyl)-2-oxo-3-(phenylsulfonamidocarbonyl)benzofuro[3,2-b]pyridine is obtained.

Example 8

Analogously to Example 1, by reaction of ethyl 4-(4-methoxyphenyl)-1,2-dihydro-2-oxobenzofuro[3,2-b]-pyridine-3-carboxylate with the following T chlorides where T is benzyl
2-trifluoromethylbenzyl
3-phenoxybenzyl
2-fluorobenzyl
2-methylbenzyl
2-cyanobenzyl
naphthylmethyl
2-trifluoromethoxybenzyl
3-trifluoromethoxybenzyl
2-methoxy-5-acetobenzyl
2-chlorobenzyl
6-fluoro-1,3-benzodioxan-8-ylmethyl
2-ethoxybenzyl
5-bromo-2-methoxybenzyl
3,4,5-trimethoxybenzyl
2,4,5-trimethoxybenzyl
2-isopropylbenzyl
3,5-dimethoxybenzyl
2,6-dimethoxybenzyl
1,4-benzodioxan-6-ylmethyl
2,1,3-benzothiadiazol-4-ylmethyl
2,4-dimethoxybenzyl
6-methoxy-1,3-benzodioxol-5-ylmethyl
6-chloro-2,1,3-benzothiadiazol-5-ylmethyl the ethyl 4-(4-methoxyphenyl)-1,2-dihydro-1-T-2-oxobenzofuro[3,2-b]pyridine-3-carboxylates below, in which T is benzyl, m.p. 183°
2-trifluoromethylbenzyl, m.p. 226°
3-phenoxybenzyl, Rf$_C$ 0.39
2-fluorobenzyl, Rf$_C$ 0.19
2-methylbenzyl, m.p. 200°
2-cyanobenzyl
naphthylmethyl, m.p. 273°
2-trifluoromethoxybenzyl, Rf$_B$ 0.4
3-trifluoromethoxybenzyl, m.p. 159°
2-methoxy-5-acetobenzyl, Rf$_C$ 0.3
2-chlorobenzyl, Rf$_C$ 0.36
6-fluoro-1,3-benzodioxan-8-ylmethyl, Rf$_B$ 0.5
2-ethoxybenzyl, Rf$_C$ 0.3
5-bromo-2-methoxybenzyl, Rf$_C$ 0.34
3,4,5-trimethoxybenzyl, Rf$_C$ 0.37
2,4,5-trimethoxybenzyl, Rf$_C$ 0.42
2-isopropylbenzyl, Rf$_C$ 0.38
3,5-dimethoxybenzyl, Rf$_C$ 0.36
2,6-dimethoxybenzyl, Rf$_C$ 0.38
1,4-benzodioxan-6-ylmethyl, Rf$_C$ 0.51
2,1,3-benzothiadiazol-4-ylmethyl, Rf$_B$ 0.36
2,4-dimethoxybenzyl
6-methoxy-1,3-benzodioxol-5-ylmethyl
6-chloro-2,1,3-benzothiadiazol-5-ylmethyl and also the ethyl 4-(4-methoxyphenyl)-2-(T-oxy)benzofuro[3,2-b]pyridine-3-carboxylates below, in which T is benzyl, m.p. 113°
2-trifluoromethylbenzyl, m.p. 101°
3-phenoxybenzyl, Rf$_C$ 0.71
2-fluorobenzyl, Rf$_C$ 0.63
2-methylbenzyl, m.p. 118°
2-cyanobenzyl
naphthylmethyl, m.p. 140°
2-trifluoromethoxybenzyl, m.p. 113°
3-trifluoromethoxybenzyl, Rf$_C$ 0.71
2-methoxy-5-acetobenzyl, m.p. 149°
2-chlorobenzyl, m.p. 115°
6-fluoro-1,3-benzodioxan-8-ylmethyl, m.p. 154°
2-ethoxybenzyl, m.p. 86°
5-bromo-2-methoxybenzyl, m.p. 147°
3,4,5-trimethoxybenzyl, m.p. 142°
2,4,5-trimethoxybenzyl, m.p. 115°
2-isopropylbenzyl, m.p. 84°
3,5-dimethoxybenzyl, m.p. 105°
2,6-dimethoxybenzyl, m.p. 141°
1,4-benzodioxan-6-ylmethyl, m.p. 146°
2,1,3-benzothiadiazol-4-ylmethyl, m.p. 172°
2,4-dimethoxybenzyl
6-methoxy-1,3-benzodioxol-5-ylmethyl
6-chloro-2,1,3-benzothiadiazol-5-ylmethyl are obtained.

Analogously to Example 2, by ester hydrolysis from the abovementioned ethyl 4-(4-methoxyphenyl)-1,2-dihydro-1-T-2-oxobenzofuro[3,2-b]pyridine-3-carboxylates, the following 4-(4-methoxyphenyl)-1,2-dihydro-1-T-2-oxobenzofuro[3,2-b]pyridine-3-carboxylic acids are obtained in which T is benzyl, m.p. 252°
2-trifluoromethylbenzyl, m.p. 294°
3-phenoxybenzyl, m.p. 183°
2-fluorobenzyl, m.p. 253°
2-methylbenzyl, m.p. 245°
2-cyanobenzyl
naphthylmethyl, m.p.>300°
2-trifluoromethoxybenzyl, m.p. 218°
3-trifluoromethoxybenzyl, m.p. 245°
2-methoxy-5-acetobenzyl, m.p. 249°
2-chlorobenzyl, m.p. 102°
6-fluoro-1,3-benzodioxan-8-ylmethyl, m.p.>300°
2-ethoxybenzyl, m.p. 239°
5-bromo-2-methoxybenzyl, m.p. 260°
3,4,5-trimethoxybenzyl, m.p. 243°
2,4,5-trimethoxybenzyl, m.p. 232°
2-isopropylbenzyl, m.p. 220°
3,5-dimethoxybenzyl, m.p. 215°
2,6-dimethoxybenzyl, m.p. 232°
1,4-benzodioxan-6-ylmethyl, m.p. 239°
2,1,3-benzothiadiazol-4-ylmethyl, m.p. 192°
2,4-dimethoxybenzyl
6-methoxy-1,3-benzodioxol-5-ylmethyl
6-chloro-2,1,3-benzothiadiazol-5-ylmethyl.

Example 9

Ethyl 8-bromo-1-(2,5-dimethoxybenzyl)-4-(4-methoxyphenyl)-1,2-dihydro-2-oxobenzofuro[3,2-b]pyridine-3-carboxylate is reacted analogously to Example 3 with phenylboronic acid to give ethyl 8-phenyl-1-(2,5-dimethoxybenzyl)-4-(4-methoxyphenyl)-1,2-dihydro-2- oxobenzofuro[3,2-b]pyridine-3-carboxylate, m.p. 216°. By ester hydrolysis thereof the 8-phenyl-1-(2,5-dimethoxybenzyl)-4-(4-methoxyphenyl)-1,2-dihydro-2-oxobenzofuro[3,2-b]pyridine-3-carboxylic acid is obtained, m.p. 270°.

Example 10

Equimolar quantities of mesyl chloride and cesium carbonate are added to a solution of ethyl 7-amino-1,2-dihydro-1-(2-methoxybenzyl)-4-(4-methoxyphenyl)-2-oxobenzofuro[3,2-b]pyridine-3-carboxylate in DMF and the mixture is stirred for one hour. After customary working up, ethyl 7-methylsulphonylamino-1,2-dihydro-1-(2-methoxybenzyl)-4-(4-methoxyphenyl)-2-oxobenzofuro-[3,2-b]pyridine-3-carboxylate is obtained.

The compounds ethyl 7-phenylsulphonylamino-1,2-dihydro-1-(2-methoxybenzyl)-4-(4-methoxyphenyl)-2-oxobenzofuro[3,2-b]-pyridine-3-carboxylate and ethyl 7-benzylsulphonylamino-1,2-dihydro-1-(2-methoxybenzyl)-4-(4-methoxyphenyl)-2-oxobenzofuro[3,2-b]-pyridine-3-carboxylate are obtained analogously.

By ester hydrolysis, the free carboxylic acids 7-methylsulphonylamino-1,2-dihydro-1-(2-methoxybenzyl)-4-(4-methoxyphenyl)-2-oxobenzofuro[3,2-b]pyridine-3-carboxylic acid, 7-phenylsulphonylamino-1,2-dihydro-1-(2-methoxybenzyl)-4-(4-methoxyphenyl)-2-oxobenzofuro[3,2-b]pyridine-3-carboxylic acid and 7-benzylsulphonylamino-1,2-dihydro-1-(2-methoxybenzyl)-4-(4-methoxyphenyl)-2-oxobenzofuro[3,2-b]pyridine-3-carboxylic acid.

The following examples relate to pharmaceutical preparations:

Example A

Injection vials

A solution of 100 g of an active compound of the formula I and 5 g of disodium hydrogen phosphate is adjusted to pH 6.5 in 3 l of double-distilled water using 2N hydrochloric acid, sterile-filtered, filled into injection vials, lyophilized under sterile conditions and aseptically sealed. Each injection vial contains 5 mg of active compound.

Example B

Suppositories

A mixture of 20 g of an active compound of the formula I is fused with 100 g of soya lecithin and 1400 g of cocoa butter, poured into moulds and allowed to cool. Each suppository contains 20 mg of active compound.

Example C

Solution

A solution of 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water is prepared. The solution is adjusted to pH 6.8, made up to 1 l and sterlized by irradiation. This solution can be used in the form of eyedrops.

Example D

Ointment 500 mg of an active compound of the formula I are mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

Example F

Coated tablets

Analogously to Example E, tablets are pressed which are then coated in a customary manner with a coating of sucrose, potato starch, talc, tragacanth, and colourant.

Example G

Capsules 2 kg of active compound of the formula I are filled into hard gelatin capsules in a customary manner such that each capsule contains 20 mg of the active compound.

Example H

Ampoules

A solution of 1 kg of active compound of the formula I in 60 l of double-distilled water is sterile filtered, filled into ampoules, lyophilized under sterile conditions and aseptically sealed. Each ampoule contains 10 mg of active compound.

What is claimed is:

1. A compound of the formula I

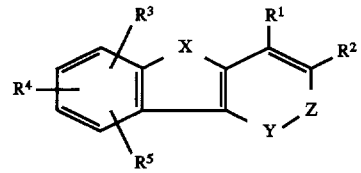

in which $-Y-Z-$ is $-NR^7-CO-$, $-N=C(OR^7)-$ or $-N=CR^8-$, $R^1$ is Ar, $R^2$ is $-COOR^6$, $-CN$, 1H-tetrazol-5-yl or $-CONHSO_2Ar$, $R^3$, $R^4$ and $R^5$ in each case independently of one another are $R^6$, $OR^6$, $S(O)_m R^6$, Hal, $NO_2$, $NR^6 R^{6'}$, $NHCOR^6$, $NHSO_2 R^6$, $OCOR^6$, $COOR^6$ or $CN$, $R^6$ and $R^{6'}$ in each case independently of one another are H, alkyl having 1 to 6 C atoms, benzyl or phenyl, $R^7$ is $(CH_2)_n Ar$, $R^8$ is Ar or OAr, Ar are in each case independently phenyl which is unsubstituted or mono-, di- or trisubstituted by $R^9$, $R^{10}$ or $R^{11}$, or unsubstituted naphthyl or

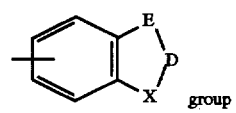

group which is unsubstituted or mono- or disubstituted in the phenyl moiety by $R^9$ or $R^{10}$ or a

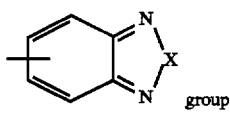 group which is unsubstituted or mono- or disubstituted in the cyclohexadienyl moiety by $R^9$ or $R^{10}$, $R^9$, $R^{10}$ and $R^{11}$ in each case independently of one another are $R^6$, $OR^6$, Hal, $CF_3$, $OCF_3$, $OCHF_2$, $OCH_2F$, $NO_2$, $NR^6R^6$, $NHCOR^6$, CN, $NHSO_2R^6$, $COOR^6$, $COR^6$, $CONHSO_2Ar$, $O(CH_2)_nR^2$, $O(CH_2)_nOR^6$ or $S(O)_mR^6$, E is $CH_2$, S or O, D is carbonyl or $[C(R^6R^{6'})]_n$, Hal is F, Cl, Br or I, X is O or S, m is 0, 1 or 2, n is 1 or 2, or a physiologically acceptable salt thereof.

2. A compound of claim 1, which compound is:
a) 1,2-Dihydro-1-(2-methoxybenzyl-4-(4-methoxyphenyl)-2-oxobenzofuro[3,2-b]pyridine-3-carboxylic acid;
b) 2-(2-methoxybenzyloxy)-4-(4-methoxyphenyl)benzofuro[3,2-b]pyridine-3-carboxylic acid;
c) 4-(1,4-benzodioxan-6-yl)-1,2-dihydro-1-(2-methoxybenzyl-2-oxobenzofuro[3,2-b]pyridine-3-carboxylic acid;
d) 2-(2-methoxyphenoxy)-4-(4-methoxyphenyl)benzofuro[3,2-b]pyridine-3-carboxylic acid;
e) 4-(1,4-benzodioxan-6-yl)-1,2-dihydro-1-(2-methoxybenzyl)-2-oxo-3-(1H-tetrazol -5-yl)benzofuro[3,2-b]pyridine;
f) 1,2-dihydro-1-(2,3-methylenedioxybenzyl)-4-(4-methoxyphenyl)-2-oxobenzofuro[3,2-b]pyridine-3-carboxylic acid;
g) 1,2-dihydro-1-(2,3-methylenedioxybenzyl)-7-methyl-4-(4-trifluoromethoxyphenyl)-2-oxobenzofuro[3,2-b]pyridine-3-carboxylic acid;
h) 1,2-dihydro-1-(2,3-methylenedioxybenzyl)-7-methyl-4-(4-methoxyphenyl)-2-oxo-benzothieno[3,2-b]pyridine-3-carboxylic acid; or
i) 1,2-dihydro-1-(2,1,3-benzothiadiazole-5-methyl)-4-(4-methoxyphenyl)-2-oxobenzofuro-[3,2-b]pyridine-3-carboxylic acid.

3. A process for the preparation of a compound of the formula I according to claim 1 or a salt thereof, comprising:
(a) for the preparation of a compound of the formula I in which —Y—Z— is —$NR^7$—CO— or —N=C($OR^7$)—, reacting a compound of the formula II

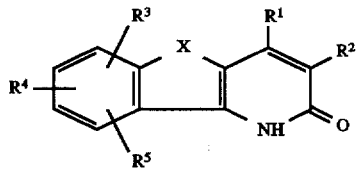

in which $R^1$, $R^2$, $R^3$, $R^4$, $R^5$ and X have the meanings indicated, with a compound of the formula III $R^7$—Q           III in which Q is Cl, Br, I or a free or reactively functionally modified OH group and $R^7$ has the meaning indicated, or (b) for the preparation of a compound of the formula I in which —Y—Z— is —N=C(Ar)—, reacting a compound of the formula IV

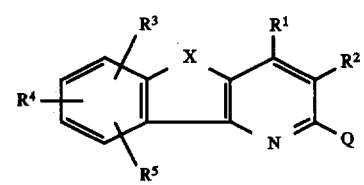

in which

Q is Cl, Br or I and $R^1$, $R^2$, $R^3$, $R^4$, $R^5$ and X have the meanings indicated, with a boron compound of the formula V Ar—BLL'           V in which L and L' in each case independently of one another are OH, $OCH_3$, $OC_2H_5$ or $OC_3H_7$, and Ar has the meaning indicated, c) for the preparation of a compound of the formula I in which —Y—Z— is —N=C(OAr)—, reacting a compound of the formula IV in which Q is Cl, Br, I or a reactively functionally modified OH group, with a compound of the formula VI Ar—OH           VI, and/or, d) in a compound of the formula I, converting one or more radicals $R^1$, $R^2$, $R^3$, $R^4$ and/or $R^5$ into one or more different radicals $R^1$, $R^2$, $R^3$, $R^4$ and/or $R^5$, and/or e) converting a base or acid of the formula I into one of its salts.

4. A pharmaceutical composition having endothelin receptor antagonist activity comprising an endothelin receptor antagonist effective amount of at least one compound of the formula I according to claim 1 and/or one of its physiologically acceptable salts.

5. A method for treating or preventing an illness treatable or preventable by endothelin receptor antagonist activity comprising administering to a patient an endothelin receptor antagonist effective amount of a composition containing a compound of the formula I of claim 1.

6. A method of claim 5, wherein the illness is treated or prevented by endothelin receptor antagonist activity effected by the composition.

7. The method of claim 5, wherein the illness is hypertension and/or cardiac insufficiency.

8. The method of claim 5, wherein the illness is hypertension; cardiac insufficiency; coronary heart disease; renal, cerebral or myocardial ischaemia; renal insufficiency; cerebral infarct; subarachnoid hemorrhage, arteriosclerosis, pulmonary high blood pressure; inflammations; asthma; prostate hyperplasia; or endotoxic shock.

9. The compound of formula I of claim 1, wherein —Y—Z— is —NR$^7$—CO— or —N=C(OR$^7$)—.

10. The compound of formula I of claim 1, wherein —Y—Z— is —N=CR$^8$—.

11. The compound of formula I of claim 1, wherein —Y—Z— is —NR$^7$—CO— and X is O.

12. The compound of formula I of claim 1, wherein —Y—Z— is —NR$^7$—CO— and X is O and Ar is a

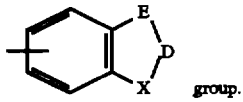 group.

13. The compound of formula I of claim 1, wherein —Y—Z— is —N=CR$^8$—,

R is Ar,

Ar is phenyl which is mono-, di- or trisubstituted by R$^9$, R$^{10}$ or R$^{11}$ and X is O.

14. The compound of formula I of claim 1, wherein X is S,

—Y—Z— is —NR$^7$—CO—,

R$^7$ is CH$_2$Ar and

Ar is a

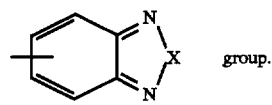 group.

15. The compound of formula I of claim 1, wherein

—Y—Z— is —N=CR$^8$—,

X is O,

Ar is a

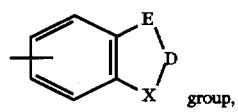 group, and

R$^8$ is OAr.

16. The method of claim 5, wherein the compound of formula I is administered in a daily dose of from approximately 0.02 to 10 mg/kg of body weight.

* * * * *